(12) United States Patent
Zhang et al.

(10) Patent No.: US 7,622,578 B2
(45) Date of Patent: Nov. 24, 2009

(54) SCALABLE PROCESS FOR THE PREPARATION OF A RAPAMYCIN 42-ESTER FROM A RAPAMYCIN 42-ESTER BORONATE

(75) Inventors: Chunhao Zhang, LaSalle (CA); Clifford William Coughlin, Plattsburgh, NY (US); Anthony Pilcher, Colchester, VT (US); Adam P. Michaud, Lawrenceville, NJ (US); James S. Farina, Warwick, NY (US); Ayman Sahli, Amman (JO)

(73) Assignee: Wyeth, Madison, NJ (US)

( * ) Notice: Subject to any disclaimer, the term of this patent is extended or adjusted under 35 U.S.C. 154(b) by 356 days.

(21) Appl. No.: 11/634,707

(22) Filed: Dec. 6, 2006

(65) Prior Publication Data

US 2007/0129541 A1 Jun. 7, 2007

Related U.S. Application Data

(60) Provisional application No. 60/748,143, filed on Dec. 7, 2005.

(51) Int. Cl.
*C07D 498/22* (2006.01)

(52) U.S. Cl. .................................................. 540/456

(58) Field of Classification Search ................... 540/456
See application file for complete search history.

(56) References Cited

U.S. PATENT DOCUMENTS

| | | | |
|---|---|---|---|
| 5,362,718 A | 11/1994 | Skotnicki et al. |
| 5,385,908 A | 1/1995 | Nelson et al. |
| 5,385,909 A | 1/1995 | Nelson et al. |
| 6,277,983 B1 | 8/2001 | Shaw et al. |
| 6,432,973 B1 | 8/2002 | Zhu et al. |
| 7,153,957 B2 | 12/2006 | Chew et al. |
| 2005/0033046 A1 | 2/2005 | Chew et al. |
| 2005/0049271 A1 | 3/2005 | Benjamin et al. |
| 2005/0234087 A1 | 10/2005 | Gu et al. |
| 2005/0234234 A1 | 10/2005 | Gu et al. |
| 2006/0036091 A1 | 2/2006 | Cai et al. |
| 2006/0135549 A1 | 6/2006 | Graziani et al. |
| 2006/0135550 A1 | 6/2006 | Graziani et al. |
| 2006/0178392 A1 | 8/2006 | Deshmukh et al. |
| 2006/0199253 A1 | 9/2006 | Shaw et al. |
| 2006/0199834 A1 | 9/2006 | Zhu |

FOREIGN PATENT DOCUMENTS

| | | |
|---|---|---|
| WO | WO-2005/016935 | 2/2005 |
| WO | WO 2005/100366 A | 10/2005 |

*Primary Examiner*—Bruck Kifle
(74) *Attorney, Agent, or Firm*—David A. Rubin; Howson & Howson LLP

(57) ABSTRACT

A scalable process for the preparation of a rapamycin 42-ester by reacting a rapamycin 42-ester boronate with a diol and purifying crude rapamycin 42-ester by recrystallization and treatment with a diol is provided. Also provided is a method for isolating and purifying a rapamycin 42-ester boronate from mother liquors comprising acetone and rapamycin contaminants.

30 Claims, No Drawings ical esters (U.S. Pat. No. 4,316,885);
SCALABLE PROCESS FOR THE PREPARATION OF A RAPAMYCIN 42-ESTER FROM A RAPAMYCIN 42-ESTER BORONATE

CROSS-REFERENCE TO RELATED APPLICATION

This application claims the benefit under 35 USC 119(e) of the priority of U.S. Provisional Patent Application No. 60/748,143, filed Dec. 7, 2005.

BACKGROUND OF THE INVENTION

Rapamycin 42-esters are derivatives of rapamycin, a macrocyclic triene antibiotic produced naturally by *Streptomyces hygroscopicus*. Rapamycin has been found useful in an array of applications based on its antitumoral and immunosuppressive effects. Such uses include preventing, inhibiting, or treating transplant rejection, graft vs. host disease, autoimmune diseases including systemic lupus erythematosis, inflammatory diseases including pulmonary and ocular inflammation, adult T cell leukemia/lymphoma, solid tumors, fungal infections, and hyperproliferative vascular disorders, including smooth muscle cell proliferation and intimal thickening following vascular surgery. Rapamycin and rapamycin derivatives, including rapamycin 42-esters such as rapamycin 42-ester with 3-hydroxy-2-(hydroxymethyl)-2-methylpropionic acid (CCI-779), continue to be studied for treatment of these and other conditions.

The preparation and use of 42-esters of rapamycin, including CCI-779, are described in U.S. Pat. No. 5,362,718. A regioselective synthesis of CCI-779 is described in U.S. Pat. No. 6,277,983. In US Patent Publication No. US 2005-0033046 A1 (also U.S. patent application Ser. No. 10/903,062), a regioselective synthesis of CCI-779 is described based on boronate chemistry.

What are needed are additional efficient methods of preparing a rapamycin 42-ester, including a scalable method for purifying the rapamycin 42-ester.

SUMMARY OF THE INVENTION

This invention provides a scalable process for preparing and purifying a rapamycin 42-ester, including rapamycin 42-ester with 3-hydroxy-2-(hydroxymethyl)-2-methylpropionic acid (CCI-779), from a rapamycin 42-ester boronate.

The preparation of a crude rapamycin 42-ester through transboronation of a rapamycin 42-ester boronate with a diol is carried out in a solvent system in which crystalline product is obtained. In one embodiment, the crude rapamycin 42-ester is purified by further treatment with a diol to reduce undesirable by-product, followed by recrystallization. In another embodiment, the crude rapamycin 42-ester produced by transboronation is recrystallized first and then a slurry of the rapamycin 42-ester is treated with a diol to provide purified rapamycin 42-ester.

Advantageously, the method of the invention avoids the use of tetrahydrofuran (THF) as a solvent, which cannot be entirely removed during manufacturing and results in an oily, sticky solid, making isolation of the rapamycin 42-ester difficult. This invention also overcomes the isolation problem associated with the use of an acetone solution of diol during the purification of rapamycin 42-esters, in which residual solvents prevent crystallization in a desired fashion and cause stability and processing problems, especially during scale-up.

Other aspects and advantages of the present invention over the prior art will be readily apparent from the following detailed description of the invention.

DETAILED DESCRIPTION OF THE INVENTION

The present invention provides a scalable process for the preparation of a rapamycin 42-ester by reacting a rapamycin 42-ester boronate with a diol and purifying the resulting crude rapamycin 42-ester by recrystallization and slurry with a diol to yield final rapamycin 42-ester. In one embodiment, the crude rapamycin 42-ester is first treated with a diol in solvent to form solid rapamycin 42-ester and then recrystallized to form purified rapamycin 42-ester. In another embodiment, the crude rapamycin 42-ester is first recrystallized to form a slurry of rapamycin 42-ester and then treated with a diol to form purified rapamycin 42-ester.

The term "a rapamycin 42-ester" includes esters of the hydroxyl group at the 42-position of rapamycin, and ethers, amides, carbonates, carbamates, sulfonates, oximes, hydrazones, and hydroxyamines of these rapamycin 42-esters in which functional groups on the nucleus have been modified, for example through reduction or oxidation, a metabolite of rapamycin such as various desmethylrapamycin or a ring opened rapamycin (such as secorapamycin, described in U.S. Pat. No. 5,252,579). The term rapamycin 42-esters also includes pharmaceutically acceptable salts of rapamycin 42-esters, which are capable of forming such salts, either by virtue of containing an acidic or basic moiety. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

A variety of 42-esters of rapamycin are described in the following patents: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). In one embodiment, rapamycin 42-esters with dicarboxylic acids, such as 42-hemisuccinate, 42-hemiglutarate and 42-hemiadipates are selected.

In one embodiment, a rapamycin 42-ester has the core structure:

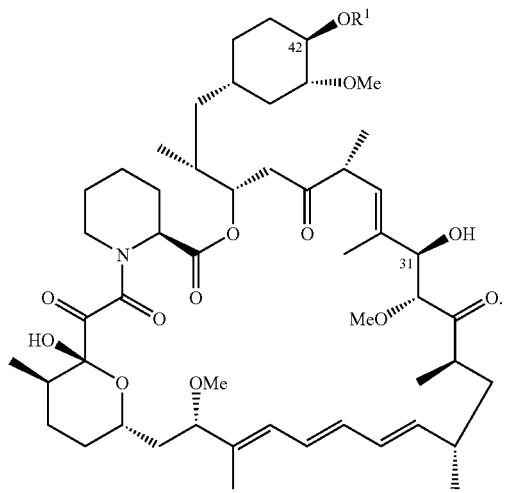

In one embodiment, $R^1$ is $-C=O.CR^7R^{7'}R^{7''}$, wherein:

$R^7$, $R^{7'}$ and $R^{7''}$ are independently selected from hydrogen, alkyl of 1-6 carbon atoms, alkenyl of 2-7 carbon atoms, alkynyl of 2-7 carbon atoms, $-(CR^{12}R^{13})_fOR^{10}$, $-CF_3$, $-F$, or $-CO_2R^{10}$;

$R^{10}$ is hydrogen, alkyl of 1-6 carbon atoms, alkenyl of 2-7 carbon atoms, alkynyl of 2-7 carbon atoms, triphenylmethyl, benzyl, alkoxymethyl of 2-7 carbon atoms, chloroethyl, or tetrahydropyranyl;

$R^{12}$ and $R^{13}$ are each, independently, hydrogen, alkyl of 1-6 carbon atoms, alkenyl of 2-7 carbon atoms, alkynyl of 2-7 carbon atoms, trifluoromethyl, or $-F$;

and f=0-6.

The compounds as described can contain one or more asymmetric centers and can thus give rise to optical isomers and diastereomers. The compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to about 8 carbon atoms (i.e., $C_1$, $C_2$, $C_3$, $C_4$, $C_5$, $C_6$, $C_7$, or $C_8$). In another embodiment, an alkyl group has 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, or $C_4$).

The term "alkenyl" is used herein to refer to both straight- and branched-chain alkyl groups having one or more carbon-carbon double bonds. In one embodiment, an alkenyl group contains 3 to about 8 carbon atoms (i.e., $C_3$, $C_4$, $C_5$, $C_6$, $C_7$, or $C_8$). In another embodiment, an alkenyl groups has 1 or 2 carbon-carbon double bonds and 3 to about 6 carbon atoms (i.e., $C_3$, $C_4$, $C_5$ or $C_6$).

The term "alkynyl" group is used herein to refer to both straight- and branched-chain alkyl groups having one or more carbon-carbon triple bonds. In one embodiment, an alkynyl group has 3 to about 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to about 6 carbon atoms (i.e., $C_3$, $C_4$, $C_5$, or $C_6$).

The term "alkoxy" as used herein refers to the O(alkyl) group, where the point of attachment is through the oxygen-atom and the alkyl group can be substituted as noted above.

In one embodiment, the rapamycin 42-ester is rapamycin 42-ester with 3-hydroxy-2-(hydroxymethyl)-2-methylpropionic acid (CCI-779) [U.S. Pat. No. 5,362,718], and 42-O-(2-hydroxy)ethyl rapamycin [U.S. Pat. No. 5,665,772]. When drawn in terms of its stereochemistry, CCI-779 is characterized by the structure:

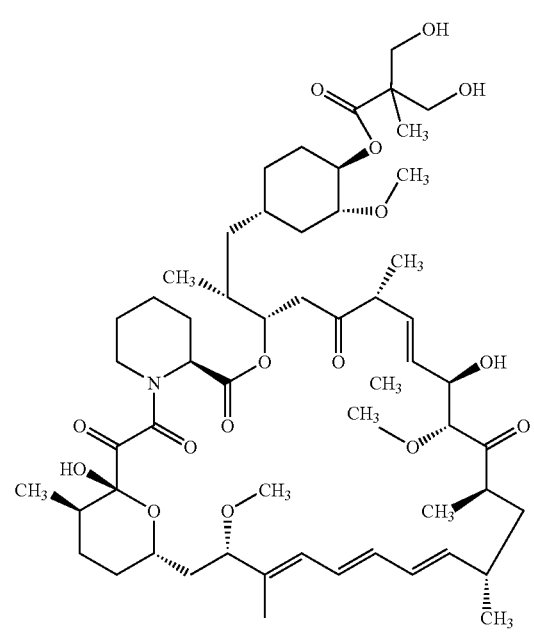

In one embodiment, the process of the invention for the preparation of a rapamycin 42-ester from rapamycin 42-ester boronate provides a yield of at least 82%, at least 85%, or at least 89% (corrected for strengths), with a strength of at least 95% or at least 98%, and total impurities of less than 4%, less than 2%, or preferably, less than 1% total impurities. As used herein, these yields are corrected for strength as follows: Yield (%)=[actual weight×strength (%)]/[theoretical weight× 100%].

In another embodiment, the rapamycin 42-ester is rapamycin 42-ester with 3-hydroxy-2-(hydroxymethyl)-2-methylpropionic acid (CCI-779). In one embodiment, the total impurities contain less than 0.1% phenylboronic acid and preferably, less than 0.05% phenylboronic acid.

The method of the invention, because it is scalable, can provide an amount of a purified rapamycin 42-ester (i.e., as defined above by freedom from total impurities) in excess of 20 kg. However, the invention is not so limited. The method is also useful in obtaining amounts of as small as 20 kg, 1 kg, 200 g, 8 g, 5 g, or smaller.

According to the present invention, crude rapamycin 42-ester is prepared from rapamycin 42-ester boronate. In one embodiment, the rapamycin 42-ester boronate used has the formula:

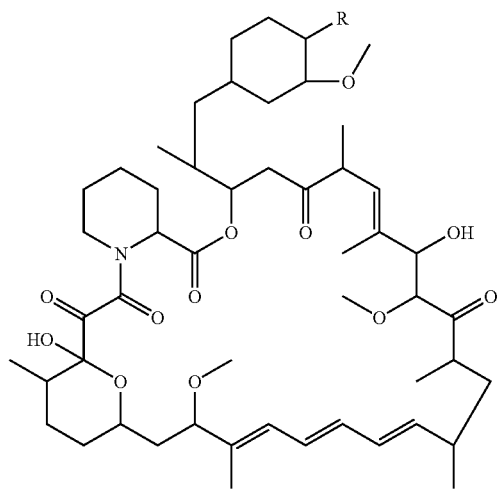

wherein R is —O—C=O.CR$^7$R$^8$R$^9$, wherein:

R$^7$ is independently selected from the group consisting of hydrogen, alkyl of 1-6 carbon atoms, alkenyl of 2-7 carbon atoms, alkynyl of 2-7 carbon atoms, —(CR$^{12}$R$^{13}$)$_f$OR$^{10}$, —CF$_3$, —F, or —CO$_2$R$^{10}$;

R$^{10}$ is hydrogen, alkyl of 1-6 carbon atoms, alkenyl of 2-7 carbon atoms, alkynyl of 2-7 carbon atoms, triphenylmethyl, benzyl, alkoxymethyl of 2-7 carbon atoms, chloroethyl, or tetrahydropyranyl;

R$^8$ and R$^9$ are taken together to form X;

X is a 2-phenyl-dioxoborinane;

R$^{12}$ and R$^{13}$ are each, independently, hydrogen, alkyl of 1-6 carbon atoms, alkenyl of 2-7 carbon atoms, alkynyl of 2-7 carbon atoms, trifluoromethyl, or —F;

and f=0-6.

As used herein, the 2-phenyl-dioxoborinane may be optionally substituted with 1, 2, or 3 groups, which are independently selected from the group consisting of hydrogen, alkyl of 1-6 carbon atoms, alkenyl of 2-7 carbon atoms, alkynyl of 2-7 carbon atoms, —(CR$^{12}$R$^{13}$)$_f$OR$^{10}$, —CF$_3$, —F, or —CO$_2$R$^{10}$. In one embodiment, the substituents are one, two or three methyl groups. The phenyl group of the 2-phenyl-dioxoborinane may also be optionally substituted.

The term "substituted aryl" refers to an aryl group (e.g., a phenyl), which is substituted with one or more substituents independently selected from including halogen, CN, OH, NO$_2$, amino, alkyl, cycloalkyl, alkenyl, alkynyl, alkoxy, C$_1$ to C$_3$ perfluoroalkyl, C$_1$ to C$_3$ perfluoroalkoxy, aryloxy, alkylcarbonyl, aryl, heteroaryl. Desirably, a substituted aryl (e.g., phenyl) group is substituted with 1 to about 4 substituents. In one embodiment, the substituent is a halogen. In another embodiment, the substituent is a lower alkyl.

In one embodiment, the 2-phenyl-dioxoborinane is selected from the group consisting of 2-phenyl-4,6,6-trimethyl-1,3,2-dioxoborinane, 2-phenyl-1,3,2-dioxaborinan-5-yl, 2-phenyl-1,3,2-dioxaborinan-4-yl, where the phenyl is optionally substituted as defined above.

In a further embodiment, the rapamycin 42-ester boronate is a boronate of rapamycin 42-ester with 3-hydroxy-2-(hydroxymethyl)-2-methylpropionic acid (CCI-779).

The rapamycin 42-ester boronate can be prepared for use in the method of the invention using previously described methods. For example, one suitable method for preparing a CCI-779 boronate is described in US Patent Publication No. US 2005-0033046 A1 (also U.S. patent application Ser. No. 10/903,062) and illustrated in scheme I.

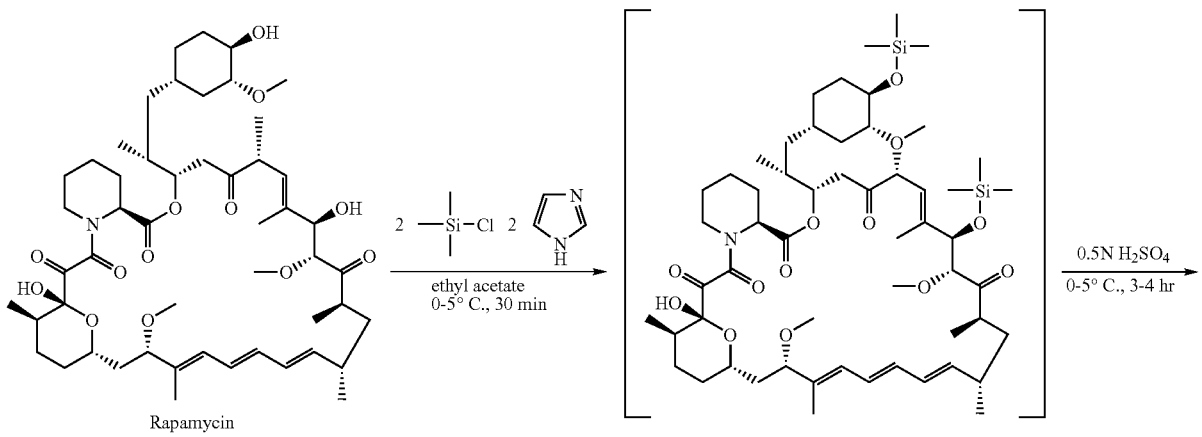

Scheme I

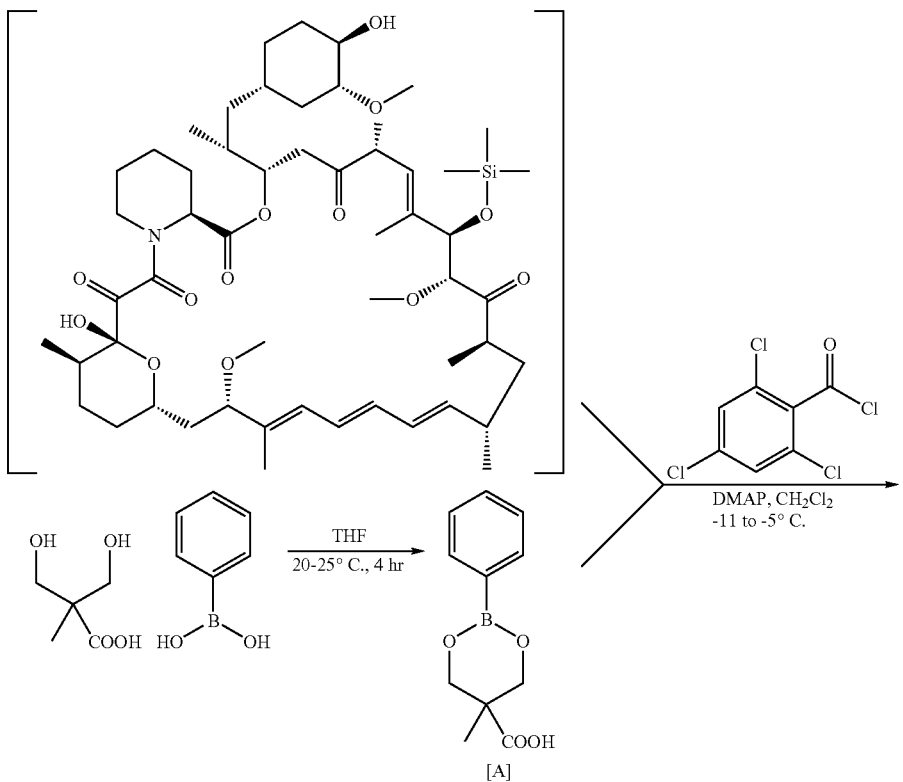
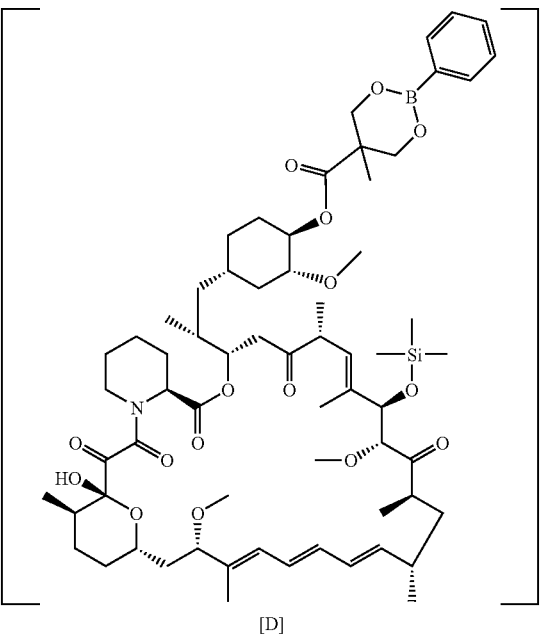
Using similar techniques, one of skill in the art can readily utilize another 31-trimethylsilyl ether, 42-ester boronate to prepare a desired 42-ester boronate. Typically, the 31-trimethylsilyl ether group is removed. Thereafter, the resulting 42-ester boronate may be purified by acetone slurry as illustrated below for CCI-779 boronate.

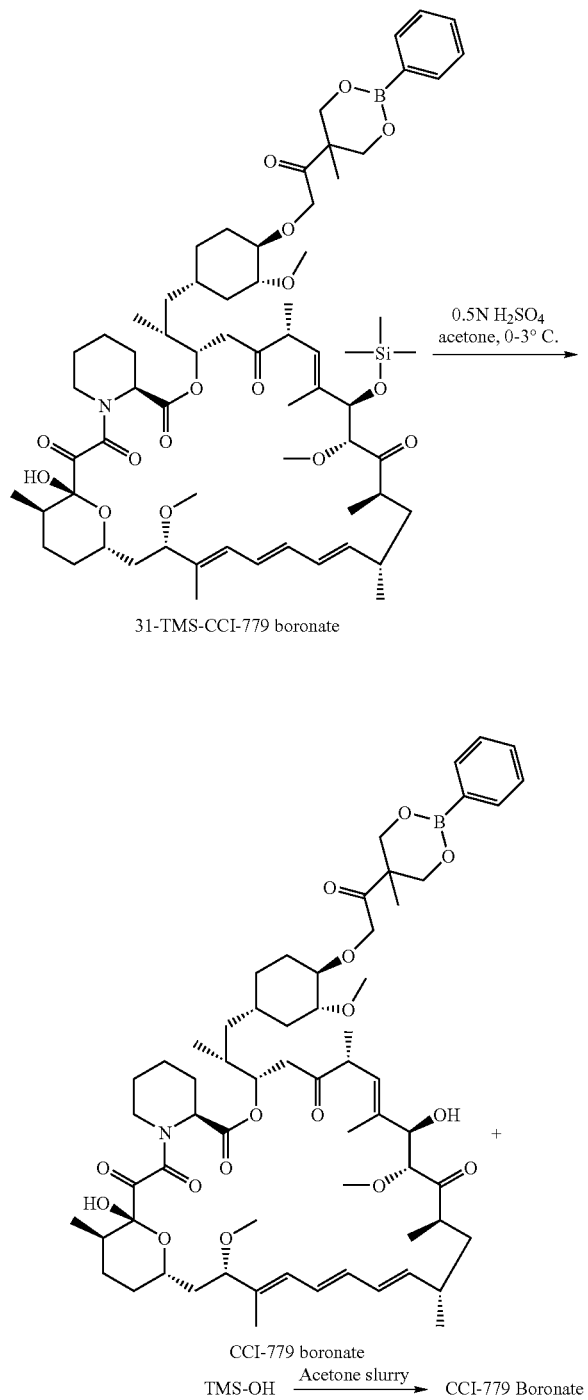

Scheme II

31-TMS-CCI-779 boronate 0.5N H₂SO₄
acetone, 0-3° C.

CCI-779 boronate

TMS-OH  Acetone slurry  CCI-779 Boronate

Given this information, one of skill in the art can readily prepare other rapamycin 42-ester boronates.

The method of preparation of a rapamycin 42-ester via a rapamycin 42-ester boronate intermediate is a route that completely eliminates chromatography from the manufacturing process. The rapamycin 42-ester boronate is prepared from rapamycin with about 80-85% conversion; however, isolated yields are significantly lower after purification by acetone slurries. In preliminary experiments, about ½ of converted materials was typically isolated.

In one embodiment, the present invention provides an improved method for isolating crude rapamycin 42-ester boronate and an improved method for purifying rapamycin 42-ester boronate for use in preparing a rapamycin 42-ester. Although this method of isolating the crude rapamycin 42-ester boronate from mother liquors is particularly well adapted for use in connection with the manufacturing process described in US 2005/0033046, published Feb. 10, 2005.

Briefly, this scalable process describes a method in which an organic solvent(s) are used in the reactions which yield a rapamycin 42-ester boronate. Such solvents may include diethyl ether, acetonitrile, ethyl acetate, THF, t-butyl methyl ether and methylene chloride may be selected. However, acetone is often used to form a concentrate. However, in certain embodiments, hydrolysis can be performed using a single phase aqueous acid/organic solvent system. Thus, the selected organic solvent (e.g., acetone) is mixed with a dilute inorganic acid such as, e.g., sulphuric, hydrochloric or phosphoric acid. Examples of suitable dilute inorganic acid concentrations range from about 0.1 N to about 3 N, about 0.2 N to about 2 N, or about 0.5 N. Desirably, this step is carried out at a pH of 5 to 6. Optionally, a suitable buffer, e.g., sodium acetate, or in the presence of sodium bicarbonate and/or acetic acid are added to the mixture to adjust or maintain the pH in the desired range. However, other methods for producing rapamycin 42-ester boronate may be utilized.

The method of isolating rapamycin 42-ester boronate permits the efficient separation of crude rapamycin 42-ester boronate from mother liquors used for production thereof. Such mother liquors typically contain the rapamycin 42-ester boronate and contaminants such as one or more solvents and rapamycin, with the largest single contaminant typically being rapamycin.

As indicated above, the method of the invention is particularly well suited for use following the acetone slurries described above. However, in one aspect, the reactors are washed with a suitable solvent and mixed with the mother liquors. Optionally, the mother liquors may be obtained from a first acetone slurry, or from mixtures of first and second acetone slurries, or from mixtures of first, second and third acetone slurries. The mother liquors may be further optionally mixed with the liquors resulting from the washing steps. Typically, the reaction wash is performed with an ether, e.g., a diethyl ether, a trimethyl ether (e.g., tri-butyl methyl ether), or the like may be selected.

Crude rapamycin 42-ester boronate is isolated from mother liquor by concentrating the mother liquor and filtering. In one embodiment, the mother liquor is concentrated to a slurry prior to filtration. Typically, this results in a higher yield, but lower quality product (e.g., about 70 to 80% w/w rapamycin 42-ester boronate, with less than or about 15 to 20% w/w contaminating rapamycin). This slurry may have a loss on drying in the range of about 15 to 30% as compared to the mother liquors from the process of Scheme II. In another embodiment, the mother liquor is concentrated to a thick slurry and diluted with an ether (e.g., diethyl ether) prior to filtration. Typically, the resulting thick slurry has a loss on drying (LOD) in the range of about 30 to about 40% as compared to the mother liquors from the first or second acetone slurry where the process of Scheme II is utilized. This method results in a higher quality product (e.g., less than or about 12 to 15% w/w rapamycin) as compared to the use of the less concentrated slurry. In yet another embodiment, the mother liquor is concentrated to a foam (i.e., a lower moisture content than the wet mass resulting from concentrating to a thick slurry), and then treated with an ether. This embodiment provides a high quality product (e.g., less than about 12% w/w, preferably less than 11% w/w, most preferably, less than 10% w/w rapamycin.

In another aspect, the invention provides for the purification of rapamycin 42-ester boronate from the isolated crude rapamycin 42-ester boronate. Desirably, the purification reduces the contaminants in the isolated crude rapamycin 42-ester boronate by at least about 10 fold. In one embodiment, the rapamycin 42-ester boronate is purified such that it contains less than 1 wt % rapamycin, preferably, about 0.8 wt % rapamycin or less. In another embodiment, the purified rapamycin 42-ester contains about 0.7 wt % rapamycin or less.

In one embodiment, the method for purifying a crude rapamycin 42-ester boronate which comprises the rapamycin 42-ester boronate, rapamycin, and possibly other contaminants (e.g., at least one solvent) involves heating a mixture comprising the crude rapamycin 42-ester boronate and a suitable solvent. The solvent is typically added in an amount in excess of the rapamycin 42-ester boronate, by weight. For example, solvent may be added in an amount of about two, three, or four times the weight of the rapamycin 42-ester boronate. Typically, the mixture is heated to reflux and held for at least about one (1) hour. The temperature and the length of holding time may be varied depending upon a variety of factors including, e.g., the solvent selected and the length of holding time desired. In one embodiment, the solvent selected is acetone and the heating temperature is about 55 to about 62° C. However, other ketones may be selected as solvents, e.g., methyl ethyl ketone. Still other solvents may include an ether (e.g., ether, diethyl ether, tributylmethyl ether (TBME), triethyl ether, etc.), acetonitrile, or mixtures thereof (e.g., acetone/ether in a ratio of 1:1 to 1:2).

Following mixing and heating, the mixture is cooled and stirred for at least about 6 hours. Typically, the mixture is allowed to cool to room temperature over time. However, it may be cooled more rapidly by suitable methods.

The mixture is concentrated to form a slurry. Following removal of at least about one third to at least about one-half of the solvent (e.g., acetone), an ether is added to the mixture, typically in about the amount of solvent removed (e.g., about 1 time to about 1.5 to about 2 times the weight of the rapamycin 42-ester boronate). However, larger or smaller amounts of solvent may be added. Conventional methods can be used to remove solvent, e.g. distillation under vacuum with or without heating. In one desirable embodiment, the ether is diethyl ether. However, other suitable ethers may be readily selected from among those described herein and well known to those of skill in the art. The resulting slurry is thereafter filtered to recover the purified rapamycin 42-ester boronate.

A first series of concentration/slurry, crystallizing, filtering steps results in improved purity of the rapamycin 42-ester boronate. However, it may be necessary to repeat the isolation procedure (e.g., distillation/slurry, crystallization, and filtration) and/or the purification procedure (e.g., reflux, concentration, crystallization, and filtration) once or twice in order to obtain a product having a desired purity, e.g., a product having less than about 1% rapamycin. In one embodiment, the product is filtered to a loss on drying of less than about 5%, preferably, less than about 3%, or less than or about 1% prior to repeating of the mixing with the solvent. Optionally, the vessel in which a first purification run was performed can be washed with ethyl acetate, and the resulting liquors subject to the isolation and/or purification methods described herein.

The resulting purified rapamycin 42-ester boronate can be used in the preparation of a rapamycin 42-ester as described herein.

Preparation of Rapamycin 42-Ester

The rapamycin 42-ester boronate is converted to a crude rapamycin 42-ester utilizing a diol in a suitable solvent, i.e., transboronation. The transboronation described herein may be accomplished for all of the rapamycin 42-ester boronate compounds encompassed by the rapamycin 42-ester boronate formula, supra. One of skill in the art will be able to readily modify the concentration of rapamycin 42-ester boronate in solvent mixture, the ratio of diol to rapamycin 42-ester boronate, solvent composition, reaction temperature, and desired reaction time, or other variable described herein, based on the rapamycin 42-ester boronate utilized.

In one embodiment, the rapamycin 42-ester boronate is provided at from about 10% to about 30%, about 15% to about 30%, about 20% to about 30%, or about 25% to about 30% by weight in solvent mixture. In a further embodiment, the rapamycin 42-ester boronate is provided at about 30% by weight. Higher concentrations of rapamycin 42-ester boronate, e.g., 40%, are not preferred as they may result in the precipitation of sticky solids which can adhere to the wall of the reactor, reducing yield. One of skill in the art would be able to select a preferred ratio based on the solvent composition, reaction temperature, and desired reaction time.

The diol is provided in the reaction mixture at a molar ratio of diol to rapamycin 42-ester boronate of from about 2:1 to about 10:1. In one embodiment, the molar ratio of diol to rapamycin 42-ester boronate is at least 5:1. In a further embodiment, the molar ratio of diol to rapamycin 42-ester boronate is about 5:1. In other embodiments, the molar ratio of diol to rapamycin 42-ester boronate is about 6:1, about 7:1, about 8:1, about 9:1, about 10:1, or any increment therein, e.g., 5.1:1 or 8.5:1. In general, increased amounts of diol promote reaction completion. One of skill in the art would be able to select a preferred ratio based on the concentration of rapamycin 42-ester boronate in solvent mixture, solvent composition, reaction temperature, and desired reaction time.

A variety of 1,2-, 1,3-, 1,4- and 1,5-diols can be used to effect this transboronation. Alkyl substituted diols are preferable such as 2-methyl-2,4-pentanediol. In another embodiment, diethanolamine or solid-supported polystyrene diethanolamine (PS-DEAM) may be utilized. Transboronation can also be achieved using carboxylic acid reagents such as oxalic, malonic, tartaric, phthalic and salicylic acid.

In one embodiment, the solvent mixture is composed of a mixture of ether and heptanes. In a further embodiment, the ether is diethyl ether. However, the invention is not so limited. In one embodiment, the solvent mixture contains ether and a single heptane. In other embodiments, the solvent mixture contains ether and a mixture of heptanes. In still other embodiments, solvents such as toluene, tert-butyl methyl ether (TBME), ethyl ether, $^i$Pr$_2$O, hexanes, cyclohexanes, dioxane, or mixtures including these solvents may be used in place of heptanes. Where reference is made herein to the use of heptanes, the use of these solvents or mixtures thereof is also contemplated.

As used herein, the term "heptanes" encompasses heptane and isomers thereof. The term also encompasses heptane preparations composed predominantly of $C_7$ isomers, with the remaining constituents primarily $C_8$ isomers, e.g., EXXSOL® Heptane Fluid (Exxon Mobil Chemical). However, the invention is not so limited. Other heptane preparations useful in the invention, including commercially available preparations, would be known to those of skill in the art and are encompassed by the present invention.

The heptanes may be selected by one of skill in the art based on reaction conditions. Further, the ratio of ether to heptanes may also be adjusted. The ratio of ether to heptanes may range from about 1:1 to about 3:1, or about 1:1 to about 2:1 by weight. While increased ratios of ether to heptanes promote reaction completion, increased ratios, e.g., 4:1, result in the precipitation of sticky solids and are therefore not preferred. In one embodiment, the ratio of ether to heptanes is about 2:1 by weight. However, one of skill in the art would be able to select a preferred ratio based on the ratio of diol to rapamycin 42-ester boronate, concentration of rapamycin 42-ester boronate in solvent mixture, solvent composition, reaction temperature, and desired reaction time.

The reaction may be carried out at temperatures ranging from about 20° C. to about 40° C., about 25° C. to about 40° C., about 30° C. to about 40° C., or about 35° C. to about 40° C., where increased temperature generally promotes reaction completion. In one embodiment, the temperature is about 30° C. to about 40° C. In a further embodiment, the temperature is about 34° C. to about 35° C. However, one of skill in the art would be able to select a preferred temperature based on the ratio of diol to rapamycin 42-ester boronate, concentration of rapamycin 42-ester boronate in solvent mixture, solvent composition, and desired reaction time.

Reaction completion may be monitored by conventional methods which are known to those of skill in the art. Under preferred conditions, the reaction may be completed efficiently within three to four hours. Following reaction completion, the crude rapamycin 42-ester produced is cooled to about 20 to 25° C. and stirred in order to avoid the formation of sticky or gummy solids. In one embodiment, the reaction mixture is stirred for about 18 hours. In another embodiment, the reaction mixture is stirred for about 38 hours. Following stirring of the reaction mixture at reduced temperature, crude rapamycin 42-ester is precipitated by the addition of a non-polar carbon-based solvent or a mixture thereof. In one embodiment, the non-polar carbon-based solvent may be hexane, pentane, and heptane, and mixtures thereof. In a further embodiment, the non-polar carbon-based solvent is heptanes. In one embodiment, the ratio of non-polar carbon-based solvent to ether is about 3:1 by weight. In one embodiment, the resulting precipitated crude rapamycin 42-ester is filtered and washed with heptanes.

Purification of Rapamycin 42-Ester

Following precipitation, the crude rapamycin 42-ester is purified by a multi-step process involving recrystallization and reaction of impurities, e.g. phenylboronic acid, with a diol. The order of these steps is not a limitation of the invention. In other words, in one embodiment, crude rapamycin 42-ester is first treated with a diol and the solid rapamycin 42-ester is recrystallized. In another embodiment, the crude rapamycin 42-ester is first recrystallized and then a slurry of the rapamycin 42-ester is treated with a diol.

The purification process described herein may be accomplished for all of the rapamycin 42-ester compounds encompassed by the rapamycin 42-ester formula, supra. One of skill in the art will be able to readily modify the concentration of rapamycin 42-ester in solvent, the ratio of diol to crude rapamycin 42-ester, solvent composition, reaction temperature, desired reaction time, or other variable described herein, based on the rapamycin 42-ester boronate utilized.

The amount of residual phenylboronic acid in crude rapamycin 42-ester prepared on large scale, e.g., above 2 kg, from rapamycin 42-ester boronate is between about 1.8 to 2.9%. Previously described methods of purification by recrystallization only reduced this amount by about half. Advantageously, the purification method of the present invention reduces the total amount of phenylboronic acid to less than 0.1%, and in some embodiments, less than 0.05%.

Purification of Crude Rapamycin 42-Ester by Diol/Recrystallization

In this embodiment, where purification by diol treatment is carried out before recrystallization, the crude rapamycin 42-ester slurry produced via transboronation is first dried of residual solvent.

The crude rapamycin 42-ester is treated with a diol in solvent. In one embodiment, the solvent is an ether. In a further embodiment, the solvent is diethyl ether. In one embodiment, the diol is 2-methyl-2,4-pentanediol. The molar ratio of diol to rapamycin 42-ester may range from about 2:1 to about 10:1. In one embodiment, the molar ratio of rapamycin 42-ester to diol is about 5:1. The reaction is carried out at about 20 to 25° C. Higher temperatures, e.g., 34° C., are not preferred as they can lead to formation of sticky solids.

Reaction completion, e.g., the disappearance of phenylboronic acid, may be monitored by conventional methods which are known to those of skill in the art. Under preferred conditions, the reaction may be completed efficiently within about five hours. In a further embodiment, the reaction may be repeated in order to further reduce the phenylboronic acid content. Following reaction completion, the partially purified rapamycin 42-ester is dried to yield solid rapamycin 42-ester.

The solid partially purified rapamycin 42-ester is dissolved in a polar solvent. In one embodiment, the solvent is acetone. In another embodiment, the solvent is ethyl acetate. However, other polar solvents may be selected by one of skill in the art, as well as appropriate ratios of solvent to crude rapamycin 42-ester. In one embodiment, the ratio of solvent to crude rapamycin 42-ester is from about 5:1 to about 8:1 (by weight). In one embodiment, the solvent is acetone and the ratio of acetone to crude rapamycin 42-ester is about 5:1 (by weight). Following dissolution of the rapamycin 42-ester, the insoluble impurities are filtered off, and the filtrate is concentrated to form a foam.

The foam is then dissolved in ether and after a period of time purified rapamycin 42-ester crystallizes out. In one embodiment, the ether is diethyl ether. However, other ethers may be used in order to precipitate the rapamycin 42-ester. In one embodiment, the ratio of rapamycin 42-ester to ether is from about 1:4 to about 1:3. In a further embodiment, the rapamycin 42-ester is about 29% to about 37%, or about 29% to about 30%, by weight in ether.

Following ether recrystallization, the resulting slurry of rapamycin 42-ester in ether may be further treated with heptanes. In one embodiment, the ratio of heptanes to ether is about 3:1 by weight. In another embodiment, following heptane treatment and isolation of the purified rapamycin 42-ester by filtration, the rapamycin 42-ester is washed with a solution of ether and heptanes prior to drying. In a further embodiment, the ratio of ether to heptanes in the wash is 1:2 by volume. Following washing, the resulting product is dried to yield the purified rapamycin 42-ester.

Purification of Crude Rapamycin 42-Ester by Recrystallization/Diol Reaction

In another embodiment, the crude rapamycin 42-ester resulting from transboronation is subjected to recrystallization first. Typically, the crude rapamycin 42-ester is filtered and dried by suction. The crude rapamycin 42-ester is then dissolved in a polar solvent, e.g., acetone or ethyl acetate, any insoluble impurities filtered, the filtrate dried to a foam and the resulting foam dissolved in polar solvent, e.g., ether. The precipitate which appears after a period of time contains the recrystallized partially purified rapamycin 42-ester.

A solution of diol in solvent is mixed with the partially purified rapamycin 42-ester to form a slurry. In one embodiment, the solvent is an ether. In a further embodiment, the solvent is diethyl ether. In one embodiment, the partially purified rapamycin 42-ester is about 10% to about 30% by weight in solvent, or about 20% to about 30% by weight in solvent. In a further embodiment, the partially purified rapamycin 42-ester is about 30% by weight in solvent.

In one embodiment, the diol is 2-methyl-2,4-pentanediol. The molar ratio of diol to rapamycin 42-ester may range from about 2:1 to about 10:1. In one embodiment, the molar ratio of rapamycin 42-ester to diol is about 5:1. The reaction is carried out at about 20 to about 25° C. Higher temperatures, e.g., 34° C., are not preferred as they can lead to formation of sticky solids Reaction completion, e.g. the disappearance of phenylboronic acid, may be monitored by conventional methods which are known to those of skill in the art. Under preferred conditions, the reaction may be completed efficiently within about five hours. In a further embodiment, the reaction may be repeated in order to further reduce the phenylboronic acid content.

Following reaction completion, heptanes are added to the mixture, and the resulting suspension is isolated by filtration and dried to yield crystalline purified rapamycin 42-ester.

In one embodiment CCI-779 produced according to the invention may be further purified according to Process for the Preparation of Purified Crystalline CCI-779 (Deshmukh, et al., U.S. Patent Application No. 60/748,006, filed Dec. 7, 2005, on the same date as the priority application in the United States Patent and Trademark Office, and its corresponding US and international application), the specification and claims of which are incorporated herein by reference. The crystallinity of CCI-779 produced according to the invention may be determined according to Method for the Measurement of Crystallinity of CCI-779 Using Differential Scanning Calorimetry (Deshmukh, et al., U.S. Patent Application No. 60/748,005, filed Dec. 7, 2005, on the same date as the priority application, and its corresponding US and international applications), the specification and claims of which are incorporated herein by reference.

The following examples are illustrative only and are not intended to

Examples 1-6 illustrate methods for isolating crude CCI-779 boronate from mother liquor from a scalable process, such as that illustrated in the following scheme.

EXAMPLE 1

Recovery of Crude CCI-779 Boronate from Mother Liquor

Isolation of crude CCI-779 boronate from the mother liquors was first evaluated using partially recovered materials of a first batch from the manufacturing process illustrated in Schemes 1 and 2 with different procedures as summarized in Table 1.

TABLE 1

| Entry | Starting mother liquor | Recovered CCI-779 boronate | Rapamycin | Balance of the materials | Recovery* |
|---|---|---|---|---|---|
| I | Mixture from 2nd and 3rd slurry | 711 grams of yellowish solids | 8% | Filtrate upon removal of solvents: 35 grams | 95 ± 5% |
| II | $1^{st}$ slurry | 471 grams of Yellow solids | 18% | Filtrate upon removal of solvents: 150 grams | 75 ± 5% |
| III | $1^{st}$ slurry | 67 grams of yellowish solids | 13% | Filtrate upon removal of solvents: 55 grams | 55 ± 5% |
| IV | $1^{st}$ slurry | 120 grams of yellowish solids | 11% | Filtrate upon removal of solvents: 220 grams | 35 ± 5% |

*Recovery = [(Recovered CCI-779 boronate/Recovered CCI-779 boronate + balance of materials) × 100%] ± 5%

As shown in entry I, crude CCI-779 boronate can be isolated by filtering the slurry obtained from concentrating a mixture of the mother liquors from $2^{nd}$ and $3^{rd}$ acetone slurries, followed by filtration. These mother liquors mainly consist of solvents, CCI-779 boronate and rapamycin. The recovery is in the range of 95±5%. Isolated CCI-779 boronate contained about 8% of rapamycin. Due to the fact that the mother liquor from the first acetone slurry contained much more impurities, three different procedures were tested.

Entry II showed results from concentrating the mother liquor to a thick slurry, followed by filtration. The recovery was in the range of 75±5% but the filtration was very slow. Crude CCI-779 boronate with about 18% rapamycin was obtained.

The second procedure (entry III) involved concentrating the mother liquor to a foam first, treating with diethyl ether to afford a slurry, followed by filtration. Crude CCI-779 boronate was isolated by filtration in 55±5% yield with a rapamycin content of 13%.

In entry IV, the mother liquor was concentrated to a thick slurry instead. After diluting with diethyl ether, the crude CCI-779 boronate was filtered. Recovery is in the range of 35±5% with a rapamycin content of 11%.

EXAMPLE 2

Purification of Crude CCI-Boronate Recovered from Mother Liquor

Table 2 summarizes results from the investigation on purification of crude CCI-779 boronate recovered from mother liquors. The rapamycin content dropped from 8.0 to 0.93% after 2 acetone slurries following the manufacturing procedure of Scheme 1.

For experimental procedure 1, the mother liquors were heated at the specified temperature for 1 h, stirred at room temperature for a minimum of 6 h, then filtered.

For experimental procedure 2A, the mother liquors were heated at the specified temperature for 1 h, cooled to room temperature over 1 h, then stirred at room temperature for a minimum of 6 h. This process was repeated 2 more times, and the resulting slurry was then filtered.

For experimental procedure 2B, the mother liquors treated with the specified solvent were heated at the specified temperature for 1 h, cooled to room temperature over 1 h, then stirred at room temperature for 30 min. This process was repeated 2 more times and the resulting slurry filtered.

For experimental procedure 3, the mother liquors with the specified solvent were heated at the specified temperature for 6 h, stirred at room temperature for a minimum of 6 h, then filtered.

For experimental procedure 4, the mother liquors with the specified solvent were stirred at room temperature for 24 h and filtered.

TABLE 2

| Process code | Solvent | T (° C.) | Yield (%) | Rapamycin (A %) in CCI-boronate crude | Rapamycin (A %) in CCI-boronate purified |
|---|---|---|---|---|---|
| 1 | Acetone | 55-60 | 68 | 8.0 | 2.3 |
| 1 | Acetone | 55-60 | 88 | 2.3 | 0.93 |
| 2A | Acetone | 55-60 | 68 | 8.0 | 1.9 |
| 2B | Acetone | 55-60 | 85 | 1.9 | 0.83 |
| 3 | Acetone | 55-60 | 66 | 8.0 | 2.2 |
| 1 | Methanol | 55-60 | 90 | 2.3 | 1.50 |
| 1 | Acetonitrile | 70-75 | 64 | 8.0 | 2.7 |
| 1 | Methyl ethyl ketone | 70-75 | 60 | 8.0 | 3.5 |
| 1 | TBME | 50-55 | 75 | 8.0 | 3.4 |
| 1 | TBME | 50-55 | 88 | 3.4 | 1.8 |
| 4 | Ether | 20-25 | 93 | 8.0 | 6.5 |
| 1 | Acetone | 55-60 | 75 | 6.5 | 1.9 |
| 1 | Acetone | 55-60 | 88 | 1.9 | 0.86 |
| 4 | Acetone/ether (1/2) | 20-25 | 86 | 8.0 | 5.8 |
| 4 | Acetone/ether (1/1) | 20-25 | 80 | 8.0 | 5.4 |
| 2B | Acetone | 55-60 | 75 | 5.8 | 1.6 |
| 4 | Ether | 20-25 | 70 | 18.0 | 11.5 |
| 4 | Ether | 20-25 | 92 | 11.5 | 11.0 |

The rapamycin content was not reduced significantly by increasing reflux and/or mixing times. Other solvents can also be used to purify the crude CCI-779 boronate, but not as efficiently as acetone. Ether can help remove some other impurities from the crude CCI-779 boronate but is not an efficient solvent for removal of rapamycin. A mixture of acetone/ether could lower both the rapamycin content and other impurities with a reasonable recovery. The rapamycin contents of close to 8% in the crude CCI-779 boronate could be reduced to 0.8% or less (specification=0.8% by 2 or 3 slurries.

EXAMPLE 3

Isolation of Crude CCI-779 Boronate from Mother Liquor

The mother liquors were concentrated and collected. The reactors were then washed with ethyl acetate. After removing solvents, the materials obtained from ethyl acetate rinses were combined with the concentrated mother liquors.

The combined mixtures were further concentrated to a thick slurry (LOD=32%, 48% for materials from mother liquors of first, second acetone slurry, respectively) before treatment with ether. Crude CCI-779 boronate was then isolated by filtration.

TABLE 3

| Entry | Mother liquor | Isolated Crude CCI-779 boronate Amounts | Rapamycin2 | LOD |
|---|---|---|---|---|
| I | First acetone slurry | 2243 g | 8.6% | 3.84% |
| II | Second acetone slurry | 890 g | 3.5% | 2.50% |

EXAMPLE 4

Purification of Crude CCI-779 Boronate from Mother Liquor

A process to recover CCI-779 boronate was designed and examined using the entire amounts of mother liquors generated from the first and second acetone slurries during purification of a manufacturing batch. Isolation of the crude CCI779 was carried out by concentrating the mother liquor to a thick slurry, followed by treatment with diethyl ether as summarized in Table 4.

More than 2 Kg of crude CCI-779 boronate with a rapamycin content of 8.6% was isolated from the mother liquor generated during first acetone slurry (Entry I). About 900 g of the crude CCI-779 boronate from mother liquor of second acetone slurry was obtained with a much lower rapamycin content (3.5%, Entry II). The crude CCI-779 boronate was purified using a modified manufacturing procedure in which a slurry of crude CCI-779 boronate in acetone is first heated at reflux similar to the manufacturing procedure. After cooling to room temperature, half of the amount of the acetone used in the slurry was replaced with diethyl ether. The resulting slurry is stirred at room temperature for a period of times and filtered.

As shown in the following table, the crude CCI779 boronate from mother liquor of the first slurry gave purified CCI-779 boronate in 59% yield with a rapamycin content of 0.8% (within specification) after two such slurries (Entry I). Recovery of the crude CCI-779 boronate from mother liquor of the second slurry was higher (70%, Rapamycin %=0.7, Entry II). A total of nearly 2 kg of purified CCI-779 boronate could be recovered [2243/1239×722 g (from ML of first slurry)+622 g (from ML of second slurry)=1929 g].

TABLE 4

| | Crude CCI-779 boronate | | Purified CCI-779 boronate | | |
|---|---|---|---|---|---|
| Entry | Amounts | Rapamycin[2] | Amounts | Yield[3] | Rapamycin[2] |
| I | 1239 g | 8.6% | 727 g | 59% | 0.8% |
| II | 890 g | 3.5% | 622 g | 70% | 0.7% |

[1]Procedure for purification: I. A slurry of crude CCI-779 boronate in acetone was stirred at reflux for 1 h, then cooled to room temperature. About half amounts of acetone were removed under vacuum. Same amounts of diethyl ether were added to thin the slurry. After stirring further for a minimum of 6 h, purified CCI-779 boronate were collected by filtration. II. Repeated I.
[2]HPLC Area %.
[3]Overall yield for two purifications.

EXAMPLE 5

Conversion of the Recovered CCI-779 Boronate into CCI-779

The recovered CCI-779 boronate (from mother liquor of first slurry) was further converted into CCI-779 using the methods described herein. As shown in Table 5, both the yield and quality of the CCI-779 isolated was comparable to those when CCI-779 boronate from another source was used. "Total Im." refers to total impurities. "LSI" refers to largest single impurity.

TABLE 5

| | | CCI-779 | | |
|---|---|---|---|---|
| Starting CCI-779 Boronate | Scale | Yield (%) | Purity/strength | Residual solvents |
| | 200 g | 86 | Strength = 99.1% | Ether = 0.12% |
| | | | Total Impurities = 1.25% | Heptanes = 0.02% |
| | | | LSI = 0.36% | |
| | | | Rapamycin = 0.42% | |
| | | | PhB(OH)$_2$ < 0.05% | |

EXAMPLE 6

Isolation and Purification of CCI-779 Boronate from Mother Liquors

A. Experiment A

The concentrated mother liquor (8.0 Kg) from the first acetone slurry of the CCI-779 boronate manufacturing process and the ethyl acetate rinses (5.5 Kg) were utilized. Solvents were removed from the ethyl acetate rinses under vacuum to give 537 g of concentrate. The concentrate was transferred using 750 mL of acetone into a 12-L multi-neck round-bottomed flask equipped with mechanical stirrer, thermometer, and distillation apparatus. About half of the concentrated mother liquor was then added to the flask. This was distilled under vacuum (28" Hg) at a pot temperature of 20-25° C. until a thick slurry was obtained. The rest of the concentrated mother liquor was added, then distilled to a thick slurry again (about 5 L). To the mixture thus obtained, 4.0 Kg of diethyl ether was added. The resulting yellow slurry was stirred for 4 h at 20-25° C. and then filtered to give 2243 g of crude CCI-779 boronate with a LOD of 3.84% (75° C./30" Hg, 2 h) and a rapamycin content of 8.6% (HPLC area %).

In a 12-L multi-neck round-bottomed flask equipped with mechanical stirrer, thermometer, and distill apparatus, was charged 1239 g of crude CCI-779 boronate and 1859 g of acetone. The volume was marked, then another 1859 g of acetone was added. The mixture was heated to reflux (56-59° C.) and held for 1 h. The slurry was cooled to 20-25° C. over 2-3 h, then distilled to the marked volume under vacuum (27" Hg) at a pot temperature of 20-25° C. 1872 g of diethyl ether was added, stirred at 20-25° C. for a minimum of 6 h, then filtered to give 865 g of crude CCI-779 boronate with a rapamycin content of 2.1%. In another 12 L multi-neck round-bottomed flask equipped with mechanical stirrer, thermometer, and distillation apparatus, was charged the entire amounts of the crude CCI-779 boronate and 1275 g of acetone. After marking the volume, another 1275 g of acetone was added. The mixture was heated with stirring at 56-59° C. for 1 h, cooled to 20-25° C. over 2-3 h, then distilled to the marked volume under vacuum (27" Hg) at a pot temperature of 20-25° C. 1275 g of diethyl ether was added, stirred for a minimum of 6 h, then filtered. After drying under vacuum (>28" Hg) at 40° C. for 5 h, 727 g of purified CCI-779 boronate (LOD=0.86) with a rapamycin content of 0.8% (HPLC area %) was obtained.

B. Experiment B

The mother liquor (221.3 Kg) from the first acetone slurry of the manufacturing batch was distilled under vacuum (42-46 torr) at a pot temperature of −5 to 25° C. until a thick slurry was obtained (about 25 L). To the mixture thus obtained, 22.1 Kg of diethyl ether was added. The resulting yellow slurry was stirred for 4 h at 19-25° C. and then filtered to give 10.1 kg of crude CCI-779 boronate. The wet cake was combined with the mother liquor (107.4 Kg) from the second acetone slurry of manufacturing batch and distilled under vacuum (22-45 torr) at a pot temperature of −1 to −9° C. until a thick slurry was obtained. To the mixture thus obtained, added 32.9 Kg of diethyl ether. The resulting yellow slurry was stirred for 4 h at 19-25° C. and then filtered. After wash twice using ether (20 kg each wash) to give 10.0 kg of CCI-779 boronate with a LOD of 0.82% (40° C./30" Hg, 2 h).

Crude CCI-779 boronate (300 g) and acetone (900 g) was charged into a flask. The mixture was heated to reflux (55 to 61° C.) and held for 1 h. The mixture was cooled to 20-25° C. over 2-3 h, then distilled to remove acetone under vacuum (23-26" Hg) at a pot temperature not exceeding 10-18° C. (final volume 940-960 mL). The diethyl ether (450 g) was added, stirred at 18-25° C. for 18 hours, and then filtered to give crude CCI-779 boronate (225 g, LOD=0.95%). The filtered crude CCI-779 boronate (224 g) and acetone (676 g) was charged into a flask. The mixture was heated to reflux (55 to 61° C.) and held for 1 h. The mixture was cooled to 19-25° C. over 2-3 h, then distilled to remove acetone under vacuum (18-20" Hg) at a pot temperature of 18-20° C. (final volume 620 mL). The diethyl ether (338 g) was added, stirred at 18-25° C. for 18 hours, and then filtered. After washing 3 times using ether (250 mL each) to give CCI-779 boronate in 63% yield (LOD=0.57%, strength=85.9%, total impurities=1.8%, LSI=0.50, rapamycin=0.95%).

Examples 7-9 illustrate one embodiment of the method of the invention for preparing purified CCI-779 from CCI-779 boronate, such as that illustrated in the Scheme III.

Scheme III

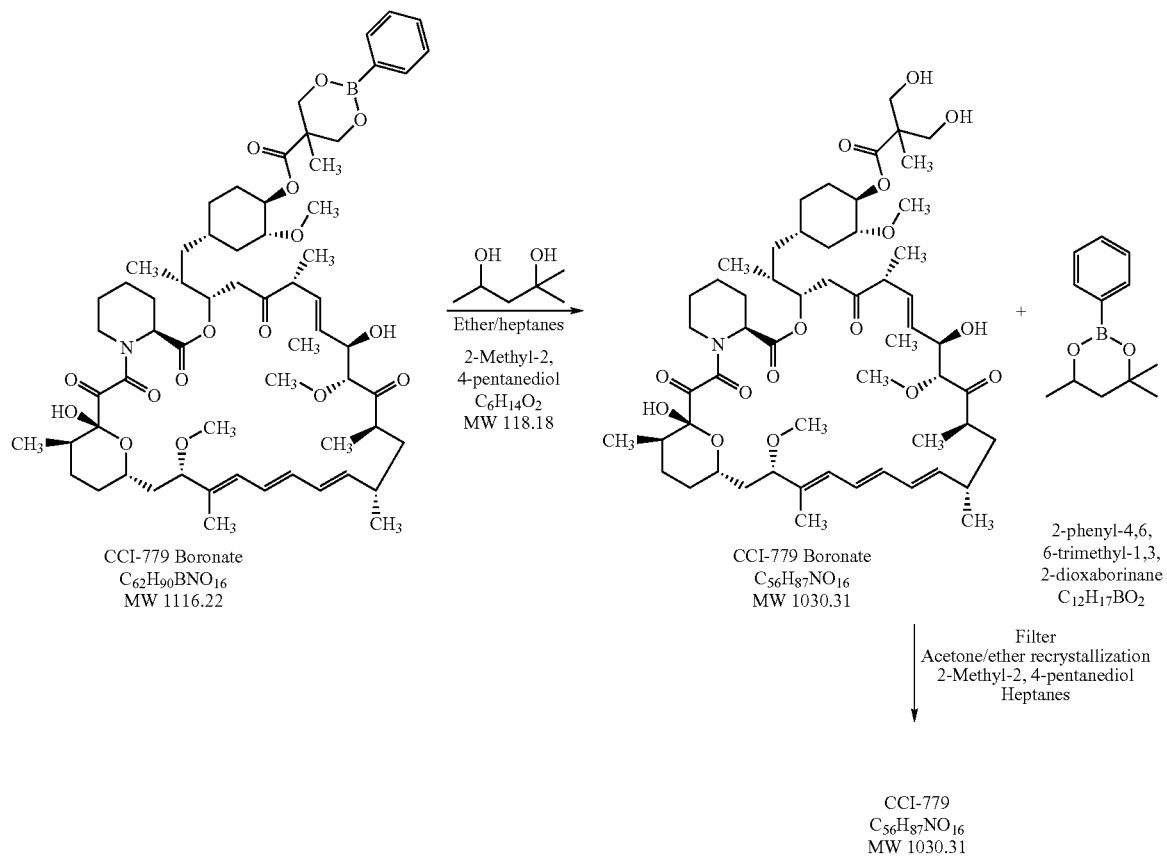

EXAMPLE 7

Preparation of Purified CCI-779

A. Preparation of Crude CCI-779

In a 3-L multi-neck round-bottomed flask equipped with mechanical stirrer, thermometer, 500-mL pressure equalizing addition funnel, and reflux condenser with a nitrogen head, was added 199 g (0.178 moles) of CCI-779 boronate, a solution of 105 g of 2-methyl-2,4-pentanediol (0.891 moles) in 371 g of diethyl ether and 185 g of heptanes. The mixture was heated to 33-37° C. with stirring under nitrogen and held for 12 h. HPLC showed the consumption of starting CCI-779 boronate (<3%) and phenylboronic acid in the reaction mixture below the specification of less than 3.0% or less than 1.5%. Cooled the reaction mixture to 20-25° C. over a 20 minutes, added 928 g of heptanes through the addition funnel over 1 h, then stirred at 20-25° C. for 1 h. The resulting mixture was filtered on a Buchner funnel. The filtered solids were washed with two portions of 500 mL of heptanes. After drying by suction until essentially no more filtrate is collected, 174 grams of crude CCI-779 was isolated [Strength=93.8%, total impurities=1.36%, rapamycin=0.40% (HPLC); ether=0.15%, heptanes=0.26% (GC)].

B. Purification of Crude CCI-779

The crude CCI-779 obtained was transferred into a 2-L flask, then 1 L of acetone was added to obtain a hazy solution. The solution was clarified through a glass Buchner funnel with a fine glass frit (4-5.5 μm). The clear filtrate was then charged to a 5-L, multi-neck flask equipped with mechanical stirrer, thermometer, and vacuum distillation apparatus. The 2-L flask and Buchner funnel were washed with 400 mL of acetone. The acetone washes were added to the 5-L flask. After the removal of acetone under a reduced pressure at 20-30° C., the foam obtained was dissolved in 420 g of diethyl ether at 20-25° C. to form a clear solution. Solids started to precipitate after 20 minutes. A solution of 105.3 g of 2-methyl-2,4-pentanediol in 52 g of diethyl ether that had been filtered through a 0.45 μm syringe filter was charged to the 5-L flask. The mixture was stirred for 1 h at 20-25° C. HPLC analysis showed that the amount of phenylboronic acid was less than 0.05%. To the reaction mixture, 1,272 g of heptanes were then added through the addition funnel over 2 h. After stirring at 20-25° C. for 1 h, the mixture was filtered on a Buchner funnel. The solids collected were washed with 3 portions of 500 mL of ether/heptanes (1/2, v/v), and suction was maintained until dripping stopped. The wet cake was dried in a vacuum oven at 50° C. under vacuum for 21 h to give 156 grams (89%, corrected for strengths) of purified CCI-779 (CZ-7781-24-2) as white crystals [Strength= 98.4%, total impurities=0.98%, rapamycin=0.36%, PhB(OH)$_2$<0.05% (HPLC); ether=0.21%, heptanes=0.037%, 2-methyl-2,4-pentanediol=0.096%, 2-methyl-2,4-pentanediol boronate=non detected (GC)].

| | | CCI-779 | |
|---|---|---|---|
| Process Code | Yield (%) | Strength/Purity (%) | Residual Solvents |
| 1 | 84 | Strength = 99.3<br>Total Im. = 0.80<br>LSI = 0.26<br>PhB(OH)$_2$ < 0.05 | n/a |
| 1 | 89 | Strength = 98.4<br>Total Im. = 0.98<br>LSI = 0.31<br>Rapamycin = 0.36<br>PhB(OH)$_2$ < 0.05<br>CCI-779 boronate = non-dect. | Ether = 0.21<br>Hept. = 0.037<br>2-methyl-2,4-pentanediol = 0.096<br>Diol-boronate = non-det. |
| 2 | 86 | Strength = 100.7<br>Total Im. = 0.92<br>LSI = 0.14<br>Rapamycin = 0.29<br>PhB(OH)$_2$ < 0.05 | Ether = 0.15<br>Hept. = 0.016<br>2-methyl-2,4-pentanediol = 0.044<br>Diol-boronate = non-det. |
| 2 | 83 | Strength = 98.7<br>Total Im. = 1.01<br>LSI = 0.26<br>Rapamycin = 0.29<br>PhB(OH)$_2$ < 0.05<br>CCI-779 boronate = non-dect. | Ether = 0.11<br>Hept. = 0.05<br>2-methyl-2,4-peanediol = 0.15<br>Diol-boronate = 0.05 |

EXAMPLE 8

Preparation of Purified CCI-779

Some early pilot studies were performed, using essentially the method described in Example 1, but with varying concentrations of CCI-779 boronate, CCI-779 prepared by different routes, and different reaction times.

In the preceding table, process code 1 refers to: 27% (wt %) CCI-779 boronate in 2/1 (wt/wt) ether/heptanes at 34-5° C. for 6-12 h, then add heptanes, filter. Purification was by acetone/ether crystallization followed by treatment with 2-methyl-2,4-pentanediol. Process code 2 refers to: 17% (wt %) CCI-779 boronate in 2/1 (wt/wt) ether/heptanes at 34-5° C. for 15-24 h, then add heptanes, filter. Purification was by acetone/ether crystallization followed by treatment with 2-methyl-2,4-pentanediol.

EXAMPLE 9

Preparation of Purified CCI-779, Alternate Route

Crude CCI-779 was prepared essentially as described above from CCI-779 boronate using 5 eq. of 2-methyl-2,4-pentanediol in a mixture of ether and heptanes (2:1, Wt/Wt) at 34° C. for 6 hours. The crude CCI-779 was isolated by filtration. The crude CCI-779 was suspended in ether, then treated with 5 eq. of 2-methyl-2,4-pentanediol, following by addition of heptanes, filtration, and drying. The dried, partially purified CCI-779 is then dissolved in acetone, clarified, and acetone removed. Following this, ether is added to crystallize product, heptanes added to the ether slurry, the slurry is filtered and dried. The resulting yield is 73% of CCI-779, having a strength of 93.5%, total impurities of less than 4% (i.e., 3.59%), and significantly, PhB(OH)$_2$ of 0.007.

All documents identified herein are incorporated by reference. One of skill in the art will recognize that minor modifications to the conditions and techniques described in the specific embodiments described herein can be varied without departing from the present invention. Such minor modifications and variants are within the scope of the invention described herein and as defined by the following claims.

The invention claimed is:

1. A process for preparing a rapamycin 42-ester, the process comprising:
   (a) reacting a rapamycin 42-ester boronate with a first diol in diethyl ether/heptanes at about 30° C. to about 40° C.;
   (b) isolating the solid from step (a);
   (c) recrystallizing the solid of (b); and
   (d) treating the product of step (c) with a second diol.

2. The process according to claim 1, wherein step (d) comprises:
   (i) treating the product of step (c) with the second diol in diethyl ether;
   (ii) collecting the solid from step (i); and
   (iii) recrystallizing the solid of step (ii) using diethyl ether/heptanes.

3. The process according to claim 1, wherein said rapamycin 42-ester boronate is isolated from mother liquor comprising rapamycin 42-ester boronate, rapamycin and one or more solvents, wherein said isolation comprises:
   (i) concentrating the mother liquor to a slurry;
   (ii) isolating the solid from step (i) using filtration.

4. The process according to claim 3, wherein the one or more solvents are selected from the group consisting of acetone, ethyl acetate, and water.

5. The process according to claim 4, further comprising:
   (i) concentrating the mother liquor comprising acetone to a foam; and
   (ii) treating the foam with diethyl ether prior to filtration.

6. The process according to claim 3, further comprising:
   (iii) treating the product of step (ii) with a solvent comprising acetone to form a second slurry prior to filtering; and
   (iv) concentrating the second slurry to form a third slurry.

7. The process according to claim 3, wherein the slurry is diluted with diethyl ether prior to filtering.

8. A method of purifying crude rapamycin 42-ester boronate from a mixture comprising the rapamycin 42-ester boronate, rapamycin, and at least one solvent, the method comprising:
   (a) heating a mixture comprising the crude rapamycin 42-ester boronate and a solvent for at least about 1 hour;
   (b) cooling the mixture of step (a);
   (c) stirring the mixture of step (b) for at least about 6 hours
   (d) concentrating the mixture of step (c) to form a concentrated slurry;
   (e) treating the mixture of step (d) with an ether;
   (f) isolating the precipitate from step (e);
   (g) purifying the product of step (f);
   (h) optionally repeating steps (a)-(g).

9. The method according to claim 8, wherein the mixture of step (b) is cooled to room temperature.

10. The method according to claim 8, wherein steps (a)-(g) are repeated at least once.

11. The method according to claim 8, wherein steps (a)-(g) are performed three times.

12. The method according to claim 11, wherein the purified rapamycin 42-ester boronate contains less than 1% by weight rapamycin.

13. The method according to claim 8, wherein the concentrated slurry of step (d) is formed by removing at least about one half of the solvent.

14. The method according to claim 8, further comprising: purifying the rapamycin 42-ester boronate isolated in step (g) by washing with a second ether.

15. The method according to claim 8, wherein the solvent is selected from the group consisting of acetone, methanol, acetonitrile, methyl ethyl ketone, TBME, ether, and mixtures thereof.

16. The method according to claim 15, wherein the solvent is acetone.

17. The method according to claim 8, wherein step (a) is performed at a temperature of about 55 to about 60° C.

18. The method according to claim 8, wherein the ether is diethyl ether.

19. The method according to claim 8, wherein step (f) is performed using filtration.

20. The method according to claim 8, wherein the rapamycin 42-ester boronate has the formula:

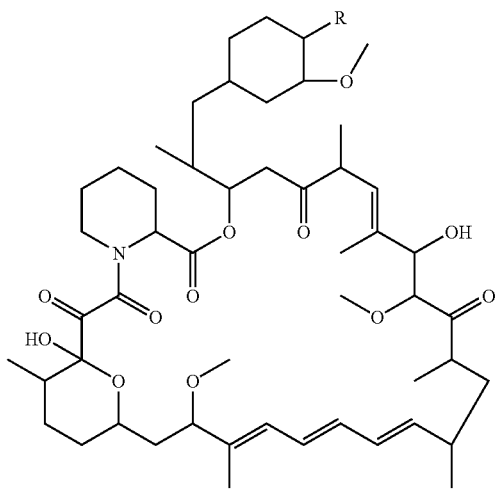

wherein:
R is —O—C=O.CR$^7$R$^8$R$^9$;
R$^7$ is selected from the group consisting of hydrogen, C$_{1-6}$ alkyl, C$_{2-7}$ alkenyl, C$_{2-7}$ alkynyl, —(CR$^{12}$R$^{13}$)$_f$OR$^{10}$, —CF$_3$, —F, and —CO$_2$R$^{10}$;
R$^{10}$ is hydrogen, C$_{1-6}$ alkyl, C$_{2-7}$ alkenyl, C$_{2-7}$ alkynyl, triphenylmethyl, benzyl, C$_{2-7}$ alkoxymethyl, chloroethyl, or tetrahydropyranyl;
R$^8$ and R$^9$ are taken together to form 2-phenyl-dioxoborinane;
R$^{12}$ and R$^{13}$ are each, independently, hydrogen, C$_{1-6}$ alkyl, C$_{2-7}$ alkenyl, C$_{2-7}$ alkynyl, trifluoromenthyl, or —F; and f=0-6.

21. A method of purifying rapamycin 42-ester with 3-hydroxy-2-(hydroxymethyl)-2-methylpropionic acid (CCI-779) boronate, the method comprising:
(a) heating to reflux a mixture comprising crude CCI-779 and a solvent comprising acetone;
(b) cooling the mixture of step (a) to room temperature;
(c) stirring the mixture of step (b) for at least about 6 hours;
(e) removing at least about half of the solvent to form a concentrated CCI-779 boronate slurry;
(e) treating the concentrated slurry of step (e) with diethyl ether;
(f) recovering the solid product of step (e); and
(g) repeating steps (a)-(f) at least once.

22. The method according to claim 21, wherein the solvent and diethyl ether in step (e) are removed under vacuum.

23. The method according to claim 21, wherein step (f) is performed by filtration.

24. A process for preparing a rapamycin 42-ester, the process comprising:
(a) reacting a rapamycin 42-ester boronate with a first diol in diethyl ether/heptanes at about 30° C. to about 40° C.;
(b) isolating the solid from step (a);
(c) treating the product of step (b) with a second diol; and
(d) recrystallizing the product of step (c).

25. The process according to claim 24, wherein the molar ratio of said first diol to rapamycin 42-ester boronate is about 5:1 to about 10:1.

26. The process according to claim 24, wherein said first diol and second diol are 2-methyl-2,4-pentanediol.

27. The process according to claim 24, wherein the product of step (a) is precipitated by the addition of one or more non-polar carbon-based solvents.

28. The process according to claim 27, wherein said non-polar carbon-based solvent is a mixture of heptanes.

29. The process according to claim 24, wherein the recrystallization comprises:
(I) dissolving the crude rapamycin 42-ester in a polar solvent; and
(II) filtering the suspension of step (I); and
(III) removing the polar solvent from the filtrate of step (III).

30. The process according to claim 24, wherein the second diol treatment comprises:
(I) mixing the crude rapamycin 42-ester in a diethyl ether; and
(II) reacting the crude rapamycin 42-ester with said second diol.

\* \* \* \* \*